United States Patent
Gomes et al.

(10) Patent No.: US 11,427,611 B2
(45) Date of Patent: Aug. 30, 2022

(54) **USE OF STEROIDAL GLYCOSIDES, PHARMACEUTICAL FORMULATIONS, USE OF *FURCRAEA FOETIDA* PLANT EXTRACTS, PROCESS FOR PRODUCING *FURCRAEA FOETIDA* PLANT EXTRACTS AND METHOD FOR TREATING SKIN DISORDERS**

(71) Applicants: Lisis Rojo Gomes, São Paulo-SP (BR); Luiz F. Pianowski, Bragança Paulista (BR)

(72) Inventors: Lisis Rojo Gomes, São Paulo-SP (BR); Luiz F. Pianowski, Bragança Paulista (BR)

( * ) Notice: Subject to any disclaimer, the term of this patent is extended or adjusted under 35 U.S.C. 154(b) by 0 days.

(21) Appl. No.: 16/635,891

(22) PCT Filed: Jun. 1, 2018

(86) PCT No.: PCT/BR2018/050181
§ 371 (c)(1),
(2) Date: Jan. 31, 2020

(87) PCT Pub. No.: WO2019/023769
PCT Pub. Date: Feb. 7, 2019

(65) Prior Publication Data
US 2021/0130392 A1    May 6, 2021

(30) Foreign Application Priority Data
Aug. 1, 2017  (BR) .......................... 1020170165507

(51) Int. Cl.
| | | |
|---|---|---|
| *C07J 71/00* | (2006.01) | |
| *A61P 17/06* | (2006.01) | |
| *A61K 31/7048* | (2006.01) | |
| *A61K 31/58* | (2006.01) | |
| *A61P 17/04* | (2006.01) | |
| *A61K 9/00* | (2006.01) | |
| *A61K 9/06* | (2006.01) | |
| *A61K 36/88* | (2006.01) | |
| *C08B 37/00* | (2006.01) | |
| *A61P 17/10* | (2006.01) | |
| *A61K 31/716* | (2006.01) | |

(52) U.S. Cl.
CPC ......... *C07J 71/0031* (2013.01); *A61K 9/0014* (2013.01); *A61K 9/06* (2013.01); *A61K 31/58* (2013.01); *A61K 31/7048* (2013.01); *A61K 31/716* (2013.01); *A61K 36/88* (2013.01); *A61P 17/04* (2018.01); *A61P 17/06* (2018.01); *A61P 17/10* (2018.01); *C07J 71/0005* (2013.01); *C08B 37/006* (2013.01); *C08B 37/0006* (2013.01); *A61K 2236/15* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 2009/0042846 A1* | 2/2009 | Gupta | A61Q 19/00 540/58 |
| 2009/0263349 A1* | 10/2009 | Story | A61P 35/04 424/85.4 |
| 2010/0048496 A1* | 2/2010 | Chibber | A61P 17/06 514/26 |
| 2012/0034193 A1 | 2/2012 | Rees et al. | |
| 2014/0274948 A1 | 9/2014 | Fasciola | |

FOREIGN PATENT DOCUMENTS

| | | |
|---|---|---|
| EP | 0020029 | 12/1980 |
| MX | 2011007842 | 1/2012 |

OTHER PUBLICATIONS

Mazumdar et al., "Evaluation of Antimicrobial Activity of Ipomoea fistulosa, Furcreae foetida, and Barleria mysorensis: An in vitro study" Research J Pharm and Tech vol. 5(8) pp. 1081-1084 (Year: 2012).*
Yokosuka et al., "Steroidal Glycosides from Furcraea foetida and Their Cytotoxic Activity" Chem Pharma Bull 57(10) 1161-1166 (2009) (Year: 2009).*
Tong et al., "*Staphylococcus aureus* Infections: Epidemiology, Pathophysiology, Clinical Manifestations, and Management" Clinical Microbiology Reviews vol. 28 No. 3 pp. 603-661 (Year: 2015).*
International Search Report dated Aug. 28, 2018 in PCT/BR2018/050181.
Sparg, et al, "Biological activities and distribution of plant saponins", 2004, pp. 219-243, vol. 94, Journal of Ethnopharmacology.

* cited by examiner

*Primary Examiner* — Eric Olson
(74) *Attorney, Agent, or Firm* — B. Aaron Schulman, Esq.; Stites & Harbison, PLLC

(57) ABSTRACT

The present invention relates, in its broadest aspects, to steroidal glycosides useful in the treatment of skin disorders. Particularly, the invention relates to the use of certain steroidal glucosides, per se, or in the form aglycona, derivatives of spirostanol, of its precursor furastanol, or mixtures thereof, used in the treatment of skin disorders, for instance, psoriasis. The invention further relates to formulations containing steroidal glycosides, the process of obtaining extract from the *Furcraea foetida* plant, and a method of treating skin disorders.

8 Claims, No Drawings

USE OF STEROIDAL GLYCOSIDES, PHARMACEUTICAL FORMULATIONS, USE OF *FURCRAEA FOETIDA* PLANT EXTRACTS, PROCESS FOR PRODUCING *FURCRAEA FOETIDA* PLANT EXTRACTS AND METHOD FOR TREATING SKIN DISORDERS

The present invention relates, in its broadest aspects, to steroidal glycosides useful in the treatment of skin disorders.

Particularly, the invention relates to the use of certain steroidal glucosides, per se, or in the form of aglycona, derivatives of spirostanol, of its precursor furastanol, or mixtures thereof, used in the treatment of skin disorders, for instance, psoriasis. The invention further relates to formulations containing steroidal glycosides, the process of obtaining extract from the *Furcraea foetida* plant, and a method of treating skin disorders.

As per mentioned herein, the following terms have the following meanings:

Glycoside: molecule in which one or more structural groups derived from sugar are linked to another functional group, through a glucosidic bond. Such structural groups derived from sugar are, in general, one or more amongst glucose, rhamnose, galactose, fucose, mannose, fructose, ribose, xylose, arabinose, and glucoronide. The glycosides of the present invention are, more particularly, without excluding any others, glucose, rhamnose and galactose.

Aglycona: non-sugar component of a steroidal glycoside.

Skin disorders: includes diseases and any abnormal dermatological condition, either by endogenous or exogenous causes.

PRIOR ART

Plant extracts are complex mixtures, which contain a variety of molecules, many of which causing effects to the animal and human organisms. Said mixtures often contain molecules that produce opposite effects—for instance, it is known that the latex of some plants contains both inflammatory and cancerous molecules, as well as molecules having anti-inflammatory and anti-cancer capabilities.

Regarding studies of the composition of mentioned plant extracts, they are typically subjected to the steps of separating their components by affinities to certain solvents, and different fractions are individually tested concerning specific effects. Such separation possibly progresses in a certain way in which it is possible to identify one or more active molecules, which alone or in conjunction provide beneficial effects.

The procedure described above is classical and allows both the detection and the obtention of natural actives important to human or animal health. Such actives can also be synthesized and modified.

In the following description, psoriasis is mentioned simply to ease the explanation, therefore, the invention should not be limited only to the abovementioned skin disorder.

The present invention relates, in a first aspect, to the use of steroidal glucosides of the Z-A type, in the preparation of formulations useful to treatment of skin disorders, in particular, to psoriasis, wherein A is a spiroestanol type structure of formula I,

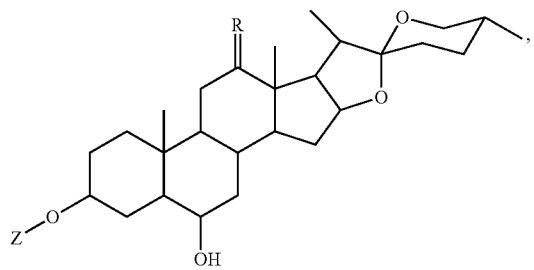

FORMULA I or a furanol type structure of formula II

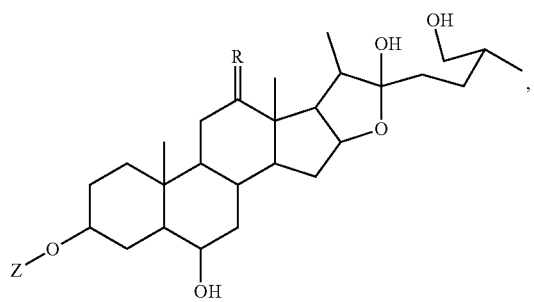

wherein R is H, H or O;
and Z represents H or one or more saccharide groups, particularly having 1 to 12 rings, more particularly having 6 rings. Such rings are, for instance, one or more amongst glucose, rhamnose, galactose, fucose, mannose, fructose, ribose, xylose, arabinose, glucoronide. In particular such rings are one or more amongst glucose, rhamnose and galactose.

Within a particular embodiment, steroidal glycosides used in the present invention are one or more amongst:

(24S,25S)-24-[(-Beta-D-glucopyranosyl)oxy]-5 alpha-spirostan-3 Beta-yl-Beta-D-glucopyranosyl-(1→3)-O-Beta-D-glucopyranosyl-(1→2)-O-[O-alpha-L-rhamnopyranosyl-(1→4 Beta D-glucopyranosyl-(1→3)]-O-Beta-D-glucopyranosyl-(1→4)-Beta-D-galactopyranoside;

(23S,25R)-6 alpha-[(Beta-D-glucopyranosyl) oxy]-23-hydroxy-5 alpha-spirostan-3 beta-D-fucoldan;

(25R)-26-[(beta-D-glucopyranosyl)) oxy]-6 alpha-hydroxy-22 alpha-methoxy -5 alpha-furoan-3 beta-yl-O-beta-D-glucopyranosyl-(1→3)-O-Beta-D-glucopyranosyl-(1→2)-O-[O-alpha-1-rhamnopyranosyl-(1→4)-beta-D-glucopyranosyl-(1→3)]-O-beta-D-glucopyranosyl-(1→4)-beta-D-galactopyranoside;

(25R)-5 alpha-spirostan-3 beta-Yl-O-Beta-D-glucopyranosyl-(1→3)-O-beta-D-glucopyranosyl-(1→2)-O-[O-alpha-1-rhamnopyranosyl-(1→4)-beta-D-Glucopyranosyl-(1→3)]-O-beta-D-glucopyranosyl-(1→4)-beta-D-galactopyranoside;

(25R)-6 alpha-hydroxy-5 alpha-spirostan-3 beta-yl O-Beta-D-glucopyranosyl-(1→3)-O-beta-D-glucopyranosyl-(1→2)-O[O-alpha-1-rhamnopyranosyl-(1→4)-beta-D-Glucopyranosyl-(1→3)]-O-beta-D-glucopyranosyl-(1→4)-beta-D-galactopyranoside;

(25R)-3 beta-[(O-Beta-D-glucopyranosyl-(1→3)-O-beta-D-glucopyranosyl-(1→2)-O[O-alpha-1-rhamnopyranosyl-(1→4)-beta-D-Glucopyranosyl-(1→3)]-O-beta-D-glucopyranosyl-(1→4)-beta-D-galactopyranosyl) oxy]-5 alpha-spirostan-12-one (furcreastatin);
(23S,25R)-3 beta, 23-dihydroxy-5 alpha-spirostan-6 alpha-yl-Beta-D-glucopyranoside;
(25R)-5 alpha-spirostane-3 beta, 6α-di-1-bis-beta-beta-D-glucopyranoside;
(23S,25R)-23-hydroxy-5 alpha-spirostane-3 beta, 6α-di-yl bis-Beta-D-glucopyranoside;
(25R)-26-[(beta-D-glucopyranosyl) oxy]-22 alpha-methoxy-5 alpha-furoan -3 beta-yl-O-beta-D-giucopyranosyl-(1→3)-O-beta-D-glucopyranosyl-(1→2)-O[O-alpha-1-rhamnopyranosyl-(1→4)-beta-D-glucopyranosyl-(1→3)]-O-beta-D-Glucopyranosyl-(1→4)-beta-D-galactopyranoside;
(25R)-3 beta-[(O-beta-D-glucopyranosyl-(1→43)-O-beta-D-glucopyranosyl -(1→2)-O[O-Alpha-1-rhamnopyranosyl-(1→4)-beta-D-glucopyranosyl -(1→3)]-O-beta-D-glucopyranosyl-(1→4)-beta-D-galactopyranosyl) oxy-26 a-[(beta-D-glucopyranosyl) oxy]-22-methoxy -5 a-furoan-12-one;
(25R)-22 alpha-methoxy-5 alpha-furoan-3 beta, 6α, 26-triyi tris-beta-D-glucopyranoside.

Particularly, A has the spatial structure of formula III

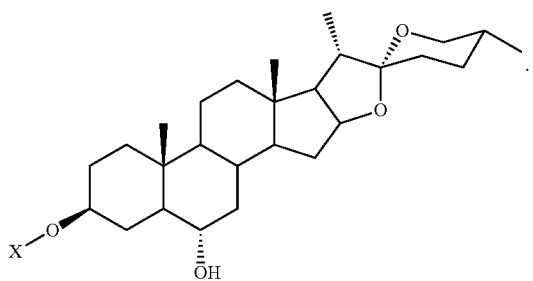

FORMULA III

Particularly, Z is a hexasaccharide, as per formula IV:

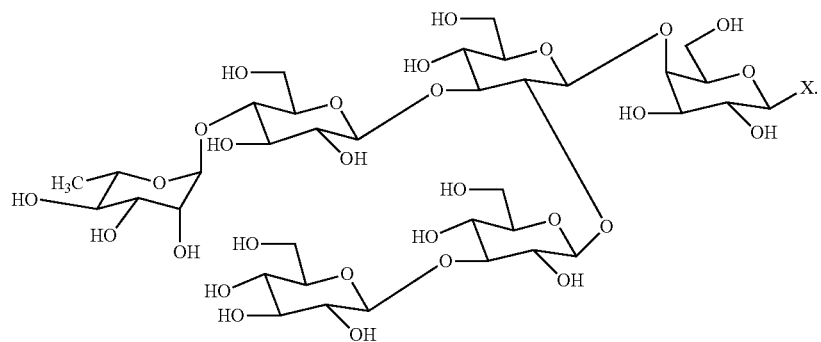

FORMULA IV

Within a particular embodiment, the steroidal glycoside Z-A used in the present invention is (25R)-6 alpha-hydroxy-5 alpha-spirostan-3 beta-yl o-beta-D-glucopyranosyl-(1→3)-o-Beta-D-glucopyranosyl-(1→2)-o-[0-alpha-1-rhamnopyranosyl-(1→4)-beta-D-glucopyranosyl-(1→3)]-o-beta-D-glucopyranosyl-(1→4)-beta-D-galactopyranoside.

In general, the skin disorders treatable with the steroidal glycosides used in the present invention are, without excluding any others, one or more amongst acne, rosacea, psoriasis, skin vesicles, sun burns, physical or chemical burns, dermatitis, eczema, skin rash, allergic reactions, fungal, bacterial and viral infections, pruritis, cellulite, urticaria, chapped lips, tattoos, waxed areas, diabetic ulcer, radiation dermatitis, scleroderma, erisiper, ictiosis decubities, cracked feet and hands.

A further aspect in the present invention relates to pharmaceutical formulations comprising one or more of the aforementioned steroidal glucosides, useful in the treatment of skin disorders, and at least one or more excipient, vehicle or carrier.

Another aspect in the present invention relates to the use of extracts from the *Furcraea foetida* plant, which contain one or more of the abovementioned steroidal glucosides used in the preparation of formulations useful in the treatment of skin disorders, particularly, psoriasis.

A further aspect of the present invention relates to the process for obtaining extracts from the *Furcraea foetida* plant, which contain one or more of the abovementioned steroidal glucosides used in the preparation of formulations useful in the treatment of skin disorders, particularly, psoriasis.

A process for obtaining extracts mentioned in the previous paragraph, comprises at least one contacting step—particularly maceration—of any parts of the *Furcraea foetida* plant (specially the leaves) with one or more carrier solvents of the steroidal glucoside(s) or saponins contained in the plant. Without excluding any other alternative, one or more of the following alcohols are examples of solvents suitable for the aforementioned extraction: ethanol, methanol, propanol, butanol, propanediol and propylene glycol, alone or in hydroalcoholic mixture, having a single-step extraction or consecutive steps. The use of suitable solvents in the present invention considers specific toxicities. The parts of the plant referred to herein are, preferably, previously milled, milled, powdered, cut, crushed or subjected to any operation capable of breaking up such parts prior to the contact with solvent. After suitable time in contact between the parts of the plant and the solvent, one or more suitable operations for solid/liquid separation are provided, for instance, filtration, decantation, centrifugation, or any other known process in the prior art. The obtained liquid from this solid/liquid separation may further, optionally be separated into distinct fractions through chromatography or any equivalent process known, by selecting the fractions containing higher levels of specific steroidal glycosides.

It is noted that the steroidal glycosides used in the present invention, as it is well-known to a person skilled in the art, can be synthetic, for instance, obtained by the synthesis of Koenigs-Knorr (W. Koenigs and E. Knorr; Chem. Ber., 1901, 34; 952) or modifications thereof (C. Meystre and K. Miescher Helv. Chim. Acta; 1944, 27, 231-236; R. B. Courow e S. Bernstein; Org. Chem. 1971, 36, 863-870; J. J. Schneider; Carbohyd. Res.; 1970, 12; 369-389; G. Wulff and G. Roehle; Angew. Chemie. 1974; 86, 173-187; N. Weber; Chem. Phys. Lipids; 1977; 18, 145-146), or by the orthoester method (N. I. Ovarova; Carbohyd. Res. 1973; 27; 79-87) by treating hydroxy-spirocetanoid 3-beta-aglycones with a brominated C-1 orthoester or with a mono- or disaccharide 1,2-orthoester acetate in the presence of silver oxide, silver carbonate or other suitable catalysts.

A further aspect of the present invention relates to a method of treating skin disorders, characterized by the administration of a pharmaceutically acceptable amount, of one or more of the abovementioned steroidal glucosides, to a subject in need of treatment.

When the treatment of skin disorders addressed by the present invention is applied through a topical via, it is characterized by placing a pharmaceutically acceptable amount, of one or more steroidal glucosides aforementioned, in contact with the skin.

The steroidal glycosides of the present invention may be natural or synthetic.

The use of the steroidal glycosides of the present invention is made through the use of formulations suitable for the intended purpose, as well-known to those persons skilled in the art. In the particular case of a topical application, such formulations may contain ingredients that are both active ingredients (in addition to the steroidal glycosides referred to herein) and pharmaceutically acceptable excipients.

The term "active principle" means a substance biologically active to the animal or human body.

Non-limiting examples of active principles that may be contained in the formulation used in the invention, besides steroidal glucosides, are one or more amongst agents with antibiotic, moisturizer, emollient, sunscreen, healing, anti-wrinkle, anti-itching, anti-inflammatory, and anti-inflammatory effects.

The term "pharmaceutically acceptable excipients" refers to substances used in pharmaceutical formulations such as diluents, carriers or additives, having no medicative activity. The following publications in the prior art are representative of sources known by those people skilled in the art concerning pharmaceutical excipients: "Remington: The Science and Practice of Pharmacy" (2000), 20th edition or later editions, Lippincott, Williams & Wilkins Publishing Company; "Pharmaceutical Dosage Forms and Drug Delivery Systems" (1999), H. C. Ansel et al., 7h edition, Lippincott, Williams & Wilkins Publishing Company; "Handbook of Pharmaceutical Excipients" (2000), A. H. Kibbe et al, 3rd edition, American Pharmaceutical Association Publishing Company.

There are no specific restrictions regarding the way the formulations which contain steroidal glycosides are administrated, as per the present invention, for instance, orally, topical, intradermic, amongst others.

Non-limiting examples of solid oral administration forms suitable to the present invention are as follows: pills, tablets, capsules, granules, pellets or powder. The powders may be lyophilized. For topical administration, the following products may be used: lotions, ointment, unguents, solutions, dispersions, emulsions, oils, etc. Other forms of administrations suitable to the present invention are liposomes and nanoparticles, or any other form well-known to a person skilled in the art.

The administrations forms suitable to the present invention may further present immediate, prolonged or controlled liberation.

Further below are examples that disclose particular embodiments related to the present invention, without, for this reason, limiting the scope, in any way, of the protection presented in the attached set of claims.

EXAMPLE 1—PROCESS FOR OBTAINING THE EXTRACT 30 parts in weight of ethanol and 70 parts in weight of *Furcraea foetida* leaves pulp, previously crushed, are blended in and left in contact together for a certain amount of time, for instance, until 48 hours. It is followed by filtration.

EXAMPLE 2—FORMULATION AND TREATMENT

The liquid of example 1 is formulated as a lotion, which is applied, periodically upon skin areas affected by psoriasis. After a few applications, it can be observed that the disease regression, both visually and concerning the pruritus, occurs in a fast and effective way.

A person skilled in the art will be able to, from the information and examples provided herein, perform the invention in equivalent forms, not expressly disclosed, however, with the same, or substantially the same function, and the same, or substantially the same results, even though they are under the protective scope of the attached set of claims.

The invention claimed is:

1. A method of treating psoriasis, comprising administering to a subject in need thereof, an effective amount of an extract from the *Furcraea foetida* plant comprising a compound of the Z-A type, wherein A is a spirostanol structure represented by Formula I

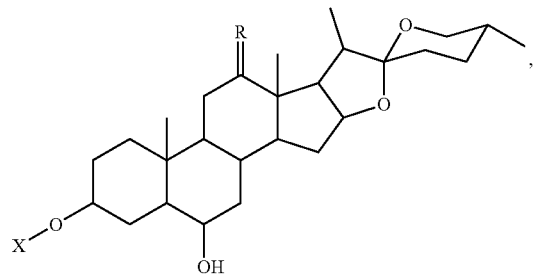

FORMULA I or a furostanol structure represented by Formula II,

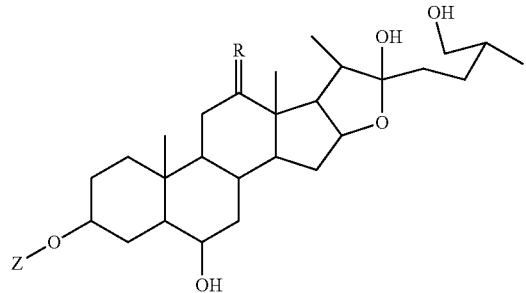

FORMULA II wherein:

R is H, H or O; and

Z is H or one or more saccharide groups having 1 to 12 rings.

2. The method of claim 1, wherein A has a spatial structure represented by Formula III

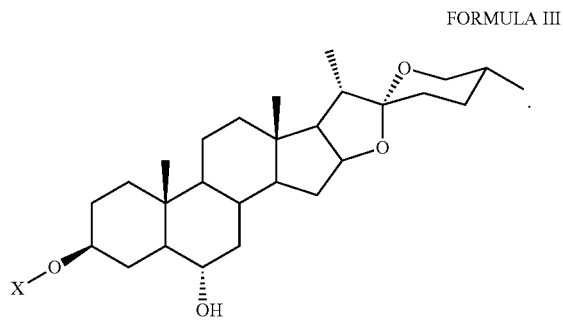

FORMULA III

3. The method of claim 1, wherein Z is one or more saccharide groups having 6 rings.

4. The method of claim 1, wherein the one or more saccharide groups is selected from the group consisting of: glucose, rhamnose, galactose, fucose, mannose, fructose, ribose, xylose, arabinose, and glucuronide.

5. The method of claim 1, wherein the steroidal glycosides are selected from the group consisting of: (24S,25S)-24-[(-beta-D-glucopyranosyl)oxy]-5 alpha-furoan-3 beta-yl-beta-D-glucopyranosyl-(1→3)-O-beta-D-glucopyranosyl -(1→2)-O-[O-alpha-L-rhamnopyranosyl-(1→4)-beta-D-glucopyranosyl-(1→3)]-O-beta -D-glucopyranosyl-(1→4)-beta-D-galactopyranoside; (23S, 25R)-6 alpha-[(Beta-D -glucopyranosyl)oxy]-23-hydroxy-5 alpha-spirostan-3 beta-D-fucoidan; (25R)-26-[(beta-D -glucopyranosyl))oxy]-6 alpha-hydroxy-22 alpha-methoxy-5 alpha-furoan-3 beta-yl-O -beta-D-glucopyranosyl-(1→3)-O-Beta-D-glucopyranosyl-(1→2)-O-[O-alpha -1-rhamnopyranosyl-(1→4)-beta-D-glucopyranosyl-(1→3)-O-beta-D-glucopyranosyl -(1→4)-beta-D-galactopyranoside; (25R)-5 alpha-spirostan-3 beta-Yl-O-Beta-D-glucopyranosyl -(1→3)-O-beta-D-glucopyranosyl-(1→2)-O-[O-alpha-1-rhamnopyranosyl-(1→4)-beta-D -Glucopyranosyl-(1→3)]-O-beta-D-glucopyranosyl-(1→4)-beta-D-galactopyranoside; (25R)-6 alpha-hydroxy-5 alpha-spirostan-3 beta-yl O-Beta-D-glucopyranosyl-(1→3)-O) -[O-alpha-L-rhamnopyranosyl-(1→4)-beta-D-glucopyranosyl-(1→3)]-O-beta-D -glucopyranosyl-(1→4)-beta-D-galactopyranoside)oxy]-5 alpha-spirostan-12-one (furcreastatin); (23S,25R)-3 beta, 23-dihydroxy-5 alpha-spirostan-6 alpha-yl-Beta -D-glucopyranoside; (25R) -5 alpha-spirostane-3 beta, 6α-di-1-bis-beta-beta-D-glucopyranoside; (23S,25R)-23-hydroxy-5 alpha-spirostane -3 beta, 6α-di-yl bis-Beta-D-glucopyranoside; (25R)-26-[(beta-D-glucopyranosyl)oxy]-22 alpha-methoxy-5 alpha-furoan-3 beta-yl-O -beta-D-glucopyranosyl-(1→3)-O-beta-D-glucopyranosyl-(1→2)-O- [O-alpha-1-rhamnopyranosyl-(1→4)-beta-D-glucopyranosyl-(1→3) ]-O-beta-D-Glucopyranosyl-(1→4)-beta-D-galactopyranoside; (25R) -3 beta-[(O-beta-D-glucopyranosyl-(1→3)-O-beta -D-glucopyranosyl-(1→2)-O-[O-Alpha-1-rhamnopyranosyl-(1→4)-beta-D-glucopyranosyl-(1 →3)]-O-beta-D-glucopyranosyl-(1→4)-beta-D-galactopyranosyl)oxy]-26 a-[(beta -D-glucopyranosyl)oxy ]-22-methoxy-5 a-furoan-12-one; (25R) -22 alpha-methoxy -5 alpha -furoan -3 beta, 6α, 26-triyl tris-beta-D-glucopyranoside; and combinations thereof.

6. The method of claim 1, wherein Z is a hexasaccharide represented by Formula IV

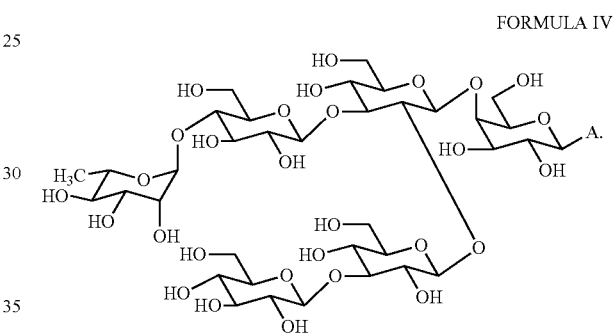

FORMULA IV

7. The method of claim 1, wherein the steroidal glycoside is (25R)-6 Alpha-hydroxy-5 Alpha-espirostan-3 beta-yl O-beta-D-glucopyranosyl-(1→3) -O-beta-D-glucopyranosyl-(1→2)-O-[O-Alpha-L-rhamnopyranosyl-(1→4)-beta-D -glucopyranosyl-(1→3)]-O-beta-D-glucopyranosyl-(1→4)-beta-D-galactopyranosyl.

8. The method of claim 1, wherein the extract is administered in the form of a pharmaceutical composition comprising the extract and a pharmaceutically acceptable carrier.

* * * * *